(12) United States Patent
Rytter et al.

(10) Patent No.: US 10,040,054 B2
(45) Date of Patent: Aug. 7, 2018

(54) FISCHER-TROPSCH SYNTHESIS (75) Inventors: Erling Rytter, Trondheim (NO); Øyvind Borg, Ranheim (NO); Sigrid Eri, Ranheim (NO); Thomas Sperle, Ranheim (NO)

(73) Assignee: GTL.FI AG, Zurich (CH)

( * ) Notice: Subject to any disclaimer, the term of this patent is extended or adjusted under 35 U.S.C. 154(b) by 1462 days.

(21) Appl. No.: 13/510,867

(22) PCT Filed: Nov. 16, 2010

(86) PCT No.: PCT/GB2010/002111
§ 371 (c)(1),
(2), (4) Date: Sep. 24, 2012

(87) PCT Pub. No.: WO2011/061484
PCT Pub. Date: May 26, 2011

(65) Prior Publication Data
US 2013/0012606 A1    Jan. 10, 2013

(30) Foreign Application Priority Data
Nov. 18, 2009 (GB) .................................. 0920226.8

(51) Int. Cl.
*B01J 23/78* (2006.01)
*B01J 23/80* (2006.01)
(Continued)

(52) U.S. Cl.
CPC ............. *B01J 21/04* (2013.01); *B01J 23/005* (2013.01); *B01J 23/75* (2013.01); *B01J 23/83* (2013.01); *B01J 23/8896* (2013.01); *B01J 23/8913* (2013.01); *B01J 23/8946* (2013.01); *B01J 35/0053* (2013.01); *B01J 35/1014* (2013.01); *B01J 35/1038* (2013.01); *B01J 35/1042* (2013.01); *B01J 37/0205* (2013.01);
(Continued)

(58) Field of Classification Search
USPC ........ 502/328, 329, 303, 327; 518/715, 717, 518/721
See application file for complete search history.

(56) References Cited

U.S. PATENT DOCUMENTS 1,746,464 A   2/1930   Fischer et al.
2,102,851 A   12/1937  La Brie
(Continued)

FOREIGN PATENT DOCUMENTS

EP   0042471   3/1981
EP   0296726   6/1988
(Continued)

OTHER PUBLICATIONS

Khassin et al., Cobalt-aluminum co-precipitated catalysts and their performance in the Fischer-Tropsch synthesis, Journal of Molecular Catalysis A: Chemical 168 (2001) 193-207.*
(Continued)

*Primary Examiner* — Colin W. Slifka
(74) *Attorney, Agent, or Firm* — Brian L. Stender; Patterson Thuente Pedersen, P.A.

(57) ABSTRACT

A process for the preparation of an F-T catalyst in which the presence of alkaline earth metals is minimized in the support itself and in the processing conditions, in order to provide a catalyst with an alkaline earth metal content of less than 2000 ppm.

46 Claims, 1 Drawing Sheet

Relative activity vs. Ca amount for all catalysts.

(51) Int. Cl.

| | | |
|---|---|---|
| *B01J 23/83* | (2006.01) | |
| *B01J 23/889* | (2006.01) | |
| *B01J 23/89* | (2006.01) | |
| *C07C 1/04* | (2006.01) | |
| *B01J 21/04* | (2006.01) | |
| *B01J 23/00* | (2006.01) | |
| *B01J 23/75* | (2006.01) | |
| *B01J 35/00* | (2006.01) | |
| *B01J 35/10* | (2006.01) | |
| *B01J 37/02* | (2006.01) | |
| *B01J 37/08* | (2006.01) | |
| *B01J 37/18* | (2006.01) | |
| *C10G 2/00* | (2006.01) | |

(52) U.S. Cl.
CPC ............ *B01J 37/0207* (2013.01); *B01J 37/08* (2013.01); *B01J 37/18* (2013.01); *C07C 1/0435* (2013.01); *C07C 1/0445* (2013.01); *C10G 2/332* (2013.01); *C10G 2/333* (2013.01); *C07C 2523/78* (2013.01); *C10G 2300/1022* (2013.01); *C10G 2300/703* (2013.01)

(56) References Cited

U.S. PATENT DOCUMENTS

| | | | |
|---|---|---|---|
| 2,548,159 | A | 4/1951 | Houtman et al. |
| 2,666,756 | A | 1/1954 | Thomas et al. |
| 2,830,877 | A | 4/1958 | Appell |
| 2,916,356 | A | 12/1959 | Keith et al. |
| 2,982,793 | A | 5/1961 | Turner et al. |
| 2,987,487 | A | 6/1961 | Stevens et al. |
| 3,025,248 | A | 3/1962 | Rosinski |
| 3,068,303 | A | 12/1962 | Pattison |
| 3,108,888 | A | 10/1963 | Bugosh |
| 3,141,742 | A | 7/1964 | Dye et al. |
| 3,235,515 | A | 2/1966 | Earl |
| 3,270,059 | A | 8/1966 | Winderl et al. |
| 3,331,787 | A | 7/1967 | Keith et al. |
| 3,344,196 | A | 9/1967 | Hubert et al. |
| 3,397,154 | A | 8/1968 | Herbert |
| 3,403,111 | A | 9/1968 | Colgan et al. |
| 3,407,149 | A | 10/1968 | Taylor et al. |
| 3,423,194 | A | 1/1969 | Kearby |
| 3,437,586 | A | 4/1969 | Weisz |
| 3,441,251 | A | 4/1969 | Burns |
| 3,565,830 | A | 2/1971 | Keith et al. |
| 3,591,649 | A | 7/1971 | Kroll et al. |
| 3,692,701 | A | 9/1972 | Box et al. |
| 3,751,508 | A | 8/1973 | Fujiso et al. |
| 3,825,504 | A | 7/1974 | Hilfman |
| 3,840,471 | A | 10/1974 | Acres |
| 3,853,790 | A | 12/1974 | Vosolsobe et al. |
| 3,876,557 | A | 4/1975 | Bland et al. |
| 3,881,696 | A | 5/1975 | Lepeytre et al. |
| 3,883,444 | A | 5/1975 | Maselli et al. |
| 3,933,883 | A | 1/1976 | Parthasarathy et al. |
| 3,966,640 | A | 6/1976 | Katz et al. |
| 3,988,263 | A | 10/1976 | Hansford |
| 4,049,582 | A | 9/1977 | Erickson et al. |
| 4,055,513 | A | 10/1977 | Wheelock |
| 4,065,484 | A | 12/1977 | Dobashi |
| 4,080,390 | A | 3/1978 | Imamura |
| 4,088,608 | A | 5/1978 | Tanaka et al. |
| 4,102,777 | A | 7/1978 | Wheelock |
| 4,102,822 | A | 7/1978 | Mulaskey |
| 4,191,664 | A | 3/1980 | McArthur |
| 4,200,552 | A | 4/1980 | Noguchi et al. |
| 4,219,444 | A | 8/1980 | Hill et al. |
| 4,233,186 | A | 11/1980 | Duprez et al. |
| 4,237,030 | A | 12/1980 | Noguchi et al. |
| 4,247,730 | A | 1/1981 | Brunelle |
| 4,285,837 | A | 8/1981 | Sato et al. |
| 4,368,142 | A | 1/1983 | Frohning et al. |
| 4,440,956 | A | 4/1984 | Couvillon |
| 4,454,207 | A | 6/1984 | Fraioli et al. |
| 4,456,703 | A | 6/1984 | Aldridge |
| 4,499,209 | A | 2/1985 | Hoek et al. |
| 4,539,310 | A | 9/1985 | Leftin et al. |
| 4,585,798 | A | 4/1986 | Beuther et al. |
| 4,595,703 | A | 6/1986 | Payne et al. |
| 4,610,975 | A | 9/1986 | Baker et al. |
| 4,613,624 | A | 9/1986 | Beuther et al. |
| 4,626,521 | A | 12/1986 | Murib |
| 4,670,414 | A | 6/1987 | Kobylinski et al. |
| 4,717,702 | A | 1/1988 | Beuther et al. |
| 4,729,981 | A | 3/1988 | Kobylinski et al. |
| 4,801,573 | A | 1/1989 | Eri et al. |
| 4,801,620 | A | 1/1989 | Fujitani et al. |
| 4,844,837 | A * | 7/1989 | Heck et al. .................. 252/373 |
| 4,857,559 | A | 8/1989 | Eri et al. |
| 4,870,044 | A | 9/1989 | Kukes et al. |
| 4,880,763 | A | 11/1989 | Eri et al. |
| 4,888,316 | A | 12/1989 | Gardner et al. |
| 4,895,816 | A | 1/1990 | Gardner et al. |
| 4,957,896 | A | 9/1990 | Matsumoto et al. |
| 4,968,660 | A | 11/1990 | Tijburg et al. |
| 4,977,126 | A | 12/1990 | Mauldin et al. |
| 4,985,387 | A | 1/1991 | Prigent et al. |
| 4,988,661 | A | 1/1991 | Arai |
| 5,037,792 | A | 8/1991 | Luck |
| 5,100,859 | A | 3/1992 | Gerdes et al. |
| 5,102,851 | A | 4/1992 | Eri et al. |
| 5,110,780 | A | 5/1992 | Peters |
| 5,116,879 | A | 5/1992 | Eri et al. |
| 5,268,091 | A | 12/1993 | Boitiaux et al. |
| 5,380,697 | A | 1/1995 | Matusz et al. |
| 5,552,363 | A | 9/1996 | Pannell et al. |
| 5,565,092 | A | 10/1996 | Pannell et al. |
| 5,565,400 | A | 10/1996 | Holmgren |
| 5,639,798 | A | 6/1997 | Wilson et al. |
| 5,744,419 | A | 4/1998 | Choudhary et al. |
| 5,851,948 | A | 12/1998 | Chuang et al. |
| 5,856,263 | A | 1/1999 | Bhasin et al. |
| 5,874,381 | A | 2/1999 | Bonne et al. |
| 5,965,481 | A | 10/1999 | Durand et al. |
| 5,977,012 | A | 11/1999 | Kharas et al. |
| 6,019,954 | A | 2/2000 | Tang et al. |
| 6,022,755 | A | 2/2000 | Kinnari et al. |
| 6,069,111 | A | 5/2000 | Yamamoto et al. |
| 6,075,062 | A | 6/2000 | Zennaro et al. |
| 6,100,304 | A | 8/2000 | Singleton et al. |
| 6,211,255 | B1 | 4/2001 | Schanke et al. |
| 6,235,798 | B1 | 5/2001 | Roy et al. |
| 6,255,358 | B1 | 7/2001 | Singleton et al. |
| 6,262,132 | B1 | 7/2001 | Singleton et al. |
| 6,271,432 | B2 | 8/2001 | Singleton et al. |
| 6,365,544 | B2 | 4/2002 | Herron et al. |
| 6,465,530 | B2 | 10/2002 | Roy-Auberger et al. |
| 6,472,441 | B1 | 10/2002 | Kibby |
| 6,486,220 | B1 | 11/2002 | Wright |
| 6,486,221 | B2 | 11/2002 | Lapidus et al. |
| 6,515,035 | B2 | 2/2003 | Roy-Auberger et al. |
| 6,537,945 | B2 | 3/2003 | Singleton et al. |
| 6,596,667 | B2 | 7/2003 | Bellusi et al. |
| 6,596,781 | B1 | 7/2003 | Schinski |
| 6,649,803 | B2 | 11/2003 | Mart et al. |
| 6,689,819 | B2 | 2/2004 | Bellussi et al. |
| 6,696,502 | B1 | 2/2004 | Mart et al. |
| 6,734,137 | B2 | 5/2004 | Wang et al. |
| 6,780,817 | B1 | 8/2004 | Koyama |
| 6,800,664 | B1 | 10/2004 | Espinoza et al. |
| 6,818,589 | B1 | 11/2004 | Gillespie |
| 6,822,008 | B2 | 11/2004 | Srinivasan et al. |
| 6,825,237 | B2 | 11/2004 | Schweitzer et al. |
| 6,835,690 | B2 | 12/2004 | Van Berge et al. |
| 6,835,756 | B2 | 12/2004 | Font Freide et al. |
| 6,927,190 | B2 | 8/2005 | Lok et al. |
| 7,012,103 | B2 | 3/2006 | Espinoza et al. |
| 7,012,104 | B2 | 3/2006 | Espinoza et al. |
| RE39,073 | E | 4/2006 | Herbolzheimer et al. |
| 7,022,644 | B2 | 4/2006 | Foong et al. |

(56) References Cited

U.S. PATENT DOCUMENTS

| | | | |
|---|---|---|---|
| 7,041,866 B1 | 5/2006 | Gillespie | |
| 7,045,554 B2 | 5/2006 | Raje et al. | |
| 7,067,562 B2 | 6/2006 | Espinoza et al. | |
| 7,071,239 B2 | 7/2006 | Ortego et al. | |
| 7,078,439 B2 | 7/2006 | Odueyungbo et al. | |
| 7,097,786 B2 | 8/2006 | Dindi et al. | |
| 7,163,963 B2 | 1/2007 | Fraenkel | |
| 7,226,574 B2 | 6/2007 | Long et al. | |
| 7,230,035 B2 | 6/2007 | Espinoza et al. | |
| 7,253,136 B2 | 8/2007 | Mauldin et al. | |
| 7,256,154 B2 | 8/2007 | Moon et al. | |
| 7,276,540 B2 | 10/2007 | Espinoza et al. | |
| 7,341,976 B2 | 3/2008 | Espinoza et al. | |
| 7,351,393 B1 | 4/2008 | Bayense et al. | |
| 7,351,679 B2 | 4/2008 | Eri et al. | |
| 7,361,626 B2 | 4/2008 | Baijense et al. | |
| 7,365,040 B2 | 4/2008 | Van Berge et al. | |
| 7,402,612 B2 | 7/2008 | Jin et al. | |
| 7,417,073 B2 | 8/2008 | Mauldin et al. | |
| 7,422,995 B2 | 9/2008 | Baijense et al. | |
| 7,452,844 B2 | 11/2008 | Hu et al. | |
| 7,473,667 B2 | 1/2009 | Hagemeyer et al. | |
| 7,541,310 B2 | 6/2009 | Espinoza et al. | |
| 7,560,412 B2 | 7/2009 | Osbourne et al. | |
| 8,143,186 B2 | 3/2012 | Rytter | |
| 8,324,128 B2 | 12/2012 | Rytter et al. | |
| 2001/0032965 A1 | 10/2001 | Wang et al. | |
| 2001/0051588 A1 | 12/2001 | Herron et al. | |
| 2002/0028853 A1 | 3/2002 | Manzer et al. | |
| 2002/0094932 A1 | 7/2002 | Faber et al. | |
| 2002/0131914 A1 | 9/2002 | Sung | |
| 2003/0119668 A1 | 6/2003 | Lok et al. | |
| 2003/0158037 A1 | 8/2003 | Foong et al. | |
| 2003/0203982 A1 | 10/2003 | Davis et al. | |
| 2004/0054016 A1 | 3/2004 | Lu et al. | |
| 2004/0077737 A1 | 4/2004 | Eri et al. | |
| 2004/0110852 A1 | 6/2004 | Srinivasan et al. | |
| 2004/0127585 A1 | 7/2004 | Raje | |
| 2004/0138060 A1 | 7/2004 | Rapier et al. | |
| 2004/0138317 A1 | 7/2004 | Xie et al. | |
| 2004/0180784 A1 | 9/2004 | Hagemeyer et al. | |
| 2004/0204506 A1 | 10/2004 | Mauldin et al. | |
| 2005/0054738 A1* | 3/2005 | Fraenkel | 518/716 |
| 2005/0184009 A1 | 8/2005 | Jansen et al. | |
| 2005/0245621 A1 | 11/2005 | Baijense et al. | |
| 2005/0272827 A1 | 12/2005 | Lok | |
| 2006/0009352 A1 | 1/2006 | Zhao et al. | |
| 2006/0167119 A1 | 7/2006 | Leng et al. | |
| 2006/0223693 A1 | 10/2006 | Fujimoto et al. | |
| 2007/0099797 A1 | 5/2007 | Hu et al. | |
| 2007/0161714 A1 | 7/2007 | Rytter et al. | |
| 2008/0064770 A1 | 3/2008 | Rytter et al. | |
| 2008/0255256 A1* | 10/2008 | Rytter | 518/715 |
| 2010/0022388 A1 | 1/2010 | Soled et al. | |
| 2010/0022670 A1 | 1/2010 | Soled et al. | |
| 2010/0029792 A1 | 2/2010 | Diehl et al. | |
| 2010/0099780 A1 | 4/2010 | Rytter et al. | |
| 2010/0184872 A1 | 7/2010 | Eri et al. | |
| 2013/0199966 A1 | 8/2013 | Koranne et al. | |

FOREIGN PATENT DOCUMENTS

| | | |
|---|---|---|
| EP | 313375 | 4/1989 |
| EP | 690119 | 6/1994 |
| EP | 1129776 | 5/2001 |
| EP | 0736326 | 8/2001 |
| EP | 1445018 | 8/2004 |
| EP | 1632289 | 3/2006 |
| GB | 1183201 | 3/1970 |
| GB | 2053712 | 2/1981 |
| GB | 2258826 | 2/1993 |
| GB | 2416715 | 2/2006 |
| JP | 58139744 | 8/1983 |
| JP | 2003024786 | 1/2003 |
| WO | WO9312879 | 7/1993 |
| WO | WO1996/00613 | 1/1996 |
| WO | WO1999/42214 | 8/1999 |
| WO | WO99/61143 | 12/1999 |
| WO | WO00/20116 | 4/2000 |
| WO | WO00/25918 | 5/2000 |
| WO | WO01/36352 | 5/2001 |
| WO | WO2002/002229 | 7/2001 |
| WO | WO01/62381 | 8/2001 |
| WO | WO02/47816 | 6/2002 |
| WO | WO02/089978 | 11/2002 |
| WO | WO03/002252 | 1/2003 |
| WO | WO04/035193 | 4/2004 |
| WO | WO2005/060448 | 7/2005 |
| WO | WO2005/072866 | 8/2005 |
| WO | WO2006/010936 | 2/2006 |
| WO | WO2006/067285 | 6/2006 |
| WO | WO2007/093825 | 8/2007 |
| WO | WO2008129034 | 10/2008 |
| WO | WO2009/118372 | 10/2009 |
| WO | WO2011027104 | 3/2011 |

OTHER PUBLICATIONS

Madikizela et al. Applied Catalysis A: General 272 (2004) 339-346).

International Search Report for International Application No. PCT/GB2008/000300 dated Jul. 25, 2008.

Betancourt, P et al., "A Study of the Ruthenium-Alumina System", Applied Catalysis A: General. vol. 170, pp. 307-314 (1998).

Van De Loosdrecht et al., "Calcination of Co-based Fischer-Tropsch Synthesis Catalysts," Topics of Catalysis, vol. 26, Nos. 1-4, pp. 121-127. (Dec. 2003).

Borg, Øyvind et al., "Effect of Calcination Atmosphere and Temperature on γ-$Al_2O_3$ Supported Colbalt Fischer-Tropsch Catalysts," Topics in Catalysis, vol. 45, Nos. 1-4, pp. 39-43 (Aug. 2007).

Schulz, "Major and Minor Reactions in Fischer-Tropsch Synthesis on Colbalt Catalysts" Topics in Catalysis, 26 91-4): 73-85 (2003).

Li Fan et al., Supercritical-phase Process for Selective Synthesis of Wax from Syngas: Catalyst and Process Development. Catalysis Today, 36:295-306/ 1997.

ASTM Standard D4058-96, 2001, "Standard Test Method for Attrition and Abrasion of Catalysts and Catalyst Carriers", ASTM Int'l. West Conshohoken, PA. Viewed on Feb. 19, 2009 at http://www.astm.org/DATABASE.CART/HISTORICAL/D4058-96R01.htm.

International Search Report for International Application No. PCT/GB2005/003675 dated Dec. 9, 2005 and GB0421242.9. dated Aug. 17, 2005.

International Search Report for International Application No. PCT/GB2005/000287 dated May 18, 2005 and GB0401829.7 dated May 6, 2005.

Iglesia et al., "Selectivity Control and Catalyst Design in the Fischer-Tropsch Synthesis: Site, Pellets and Reactors", Advances in Catalysis, vol. 3. (1993).

Saib et al., "Silica supported colbalt Fischer-Tropsch catalysts: Effect of Pore Diameter of Support", Catalysis Today, 71: 395-402 (2002).

Tang et al., "Partial Oxidation of Methane of Synthesis Gas Over Alpha-AL2O3-Supported Bimetallic Pt—Co Catalysts", Catalysis Letters, Baltzer, Scientific Publ. Basel, CH. vol. 59, No. 2/4. Jun. 1999. pp. 129-135.

Oukaci et al., "Comparison of patented Co. F-T catalysts using fixed-bed and slurry bubble column reactors" Applied Catalysis A: General Elsevier Scienc, Amsterdamn, NL, vol. 186, No. 1-2. Oct. 4, 1999, pp. 120-144.

Iglesia et al., "Reactions-Transport Selectivity Models and the Design of Fischer-Tropsch Catalysts," Computer-Aided Design of Catalysts, Edited by Becker and Pereira. Ch. 7. pp. 199-257. 1993.

Jacobs et al, "Fischer-Tropsch Synthesis XAFS XAFS studies of the effect of water on a PT-promoted Ca/$Al_2O_3$ catalyst", Applied Catalysis, 247:335-343. (2003).

International Search Report for International Application No. PCT/GB2010/002111 dated May 25, 2012.

International Search Report for International Application No. PCT/GB01/05461 dated Mar. 1, 2002.

(56) References Cited

OTHER PUBLICATIONS

International Search Report for International Application No. PCT/GB03/04873 dated Mar. 25, 2004.
International Search Report for International Application No. PCT/GB2010/001647 dated Nov. 2, 2010.
Luo et al., "Fischer-Tropsch Synthesis: Group II alkali-earth metal promoted catalysts", Applied Catalysis. pp. 171-181 (2003).
Compressed Air and Gas Institute (What is Clean, Dry Air?) TAP #106, published Nov. 1, 2005.
Stevens et al., Qatar Fertilizer Company, in the proceedings of Nitrogen + Syngas 2008 conference conducted in Moscow, pp. 20-23. Apr. 2008.
Catalyst Handbook, 2nd edition, M.V. Twigg, editor Wolfe Publishing, London 1989. pp. 77-81.
Application and File History for U.S. Appl. No. 10/433,846, filed Nov. 10, 2003, inventors Eri et al.
Application and File History for U.S. Appl. No. 10/535,066, filed Mar. 15, 2006, inventors Rytter et al.
Application and File History for U.S. Appl. No. 10/587,825, Feb. 2, 2007 inventors Rytter et al.
Application and File History for U.S. Appl. No. 11/663,663, filed Feb. 14, 2008, inventor Rytter.
Application and File History for U.S. Appl. No. 12/525,070, filed Mar. 26, 2010, inventors Eri et al.
Application and File History for U.S. Appl. No. 12/582,541, filed Oct. 20, 2009, inventor Rytter et al.
Application and File History for U.S. Appl. No. 13/378,581, filed Dec. 15, 2011, inventors Rytter et al.
Satterfield., "Heterogenous Catalysis of Practice". McGraw-Hill. (1980) p. 79.
Gates et al., "Chemistry of Catalytic Processes", (1979) p. 250.
Chorkendorff et al., "Concepts of Modern Catalysis and Kinetics", 2nd Edition. Wiley-VCH Werlage DmbH & Co. (2007). p. 194.
deKlerk et al., "Catalysis in the Refining of Fischer-Tropsch Syncrude", Royal Society Chemistry. (2010) pp. 11 and 15.
Application and File History for U.S. Appl. No. 13/814,905, filed Apr. 19, 2013, inventors Koranne et al.
Taylor, "An Introduction to Error Analysis", 2nd Ed. (1997). 329 pages. Chs. 1 and 2 provided.
Dancuart et al., "Studies in Surface Science and Catalysis". (2007). 163, 379-399.

\* cited by examiner

Relative activity vs. Ca amount for all catalysts.

FISCHER-TROPSCH SYNTHESIS

RELATED APPLICATIONS

The present application is a National Phase entry of PCT Application No. PCT/GB2010/002111, filed Nov. 16, 2010, which claims priority from Great Britain Application No. 0920226.8, filed Nov. 18, 2009, the disclosures of which are hereby incorporated by reference in their entireties.

TECHNICAL FIELD

The present invention is concerned with cobalt-based catalysts, in particular, supported Co-based catalysts and a process for its synthesis. A variety of products can be made by the Fischer-Tropsch (FT)-reaction, but from supported cobalt, the primary product is long-chain hydrocarbons that can be further upgraded to products like diesel fuel and petrochemical naphtha. Byproducts can include olefins and oxygenates.

BACKGROUND OF THE INVENTION

The FT-reaction for conversion of synthesis gas, a mixture of CO and hydrogen, possibly also containing essentially inert components like $CO_2$, nitrogen and methane, is commercially operated over catalysts containing the active metals iron (Fe) or cobalt (Co). However, the iron catalysts exhibit a significant shift reaction, producing more hydrogen in addition to $CO_2$ from CO and steam. Therefore, the iron catalyst will be most suited for synthesis gas with low $H_2/CO$ ratios (<1.2) e.g. from coal or other heavy hydrocarbon feedstock, where the ratio is considerably lower than the consumption ration of the FT reaction (2.0-2.1).

Normally, the active FT metal is dispersed on a solid, porous support. Thereby, a large portion of the Co is exposed as surface atoms where the reaction can take place. The support can be alumina, titania or silica, but generally speaking, other oxides like zirconia, magnesia, silica-alumina, various aluminates, zeolites as well as carbon, and mixtures thereof, have been used. Sometimes the support contains modifying components ingredients, e.g. of compounds of silicon, lanthanum, titanium and zirconium.

To enhance the catalyst performance, e.g. by facilitating reduction of cobalt oxide to cobalt metal prior to the FT synthesis, it is common to add different promoters, and rhenium, ruthenium, platinum, iridium and other transition metals can all be beneficial. Alternatively, the promoter may be alkali metals or alkaline earth metals. It has been discovered that certain amounts of alkali metals (K, Na, Cs, Rb, Li, Cs) have a significant impact on the catalytic performance of cobalt supported catalysts. U.S. Pat. No. 4,880,763 (Eri et al) reported that addition of an alkali to the catalyst serves to increase the average molecular weight of the product, as shown by an increase in the Schulz-Flory α value. However, the activity decreased as the alkali content increased. Thus, for any particular situation, there is an optimum alkali level that balances the desired average product molecular weight and catalyst activity. In WO2006/010936 A1, Rytter and Eri described the effect of Na on cobalt catalysts. A clear, negative effect on the activity was discovered in the range 0 to 500 ppm.

Luo and Davis (Fischer-Tropsch synthesis: Group II alkali-earth metal promoted catalysts, Appl. Catal. A 246 (2003) 171) compared the effect of alkaline earth metals, among them calcium, on the Fischer-Tropsch synthesis performance over an iron-based catalyst in a continuous stirred tank reactor (CSTR). They found that the addition of calcium as a promoter has a negative effect on the activities of both Fischer-Tropsch synthesis and the water-gas shift reaction. However, Ca generated a higher FTS alpha value (chain growth probability) than the un-promoted catalysts.

An FT catalyst is operated in an industrial process in which synthesis gas (syngas; a gas mixture of $H_2$ and CO which possibly also can contain other gases e.g. $CO_2$, $CH_4$, light hydrocarbons, steam, $N_2$ etc.) is converted to hydrocarbons by the FT-process. Syngas can be prepared in a number of ways such as autothermal reforming (ATR), methane steam reforming (MSR) sometimes called tubular reforming, partial oxidation (POx), catalytic partial oxidation (CPO) and gasification. The latter is primarily used for other feeds than natural gas, typically coal or biomass. Combinations and optimizations of these processes are also possible, as in combined reforming, heat exchanged reforming, compact reforming and gas heated reforming.

Following syngas generation, frequently the gas is cooled down in a waste heat boiler (WHB), also called process gas cooler, and further energy can be extracted from the gas by using a superheater to enhance the temperature in generated steam. Before the gas enters the FT-reactor, the gas may be cleaned of impurities like ammonia and sulphur and various carbonyl compounds using guard beds. Both in the syngas generation and in the cleaning process, refractory or ceramic materials are frequently employed. These can consist of mixtures of various metal oxides. It has now been discovered that great care must be taken as to the composition of these materials.

In Catalyst Handbook (Catalyst Handbook, $2^{nd}$ edition, M. V. Twigg, editor, Wolfe Publishing, London 1989), poisoning by impurities is described on pages 77-81. However, the effect of calcium is not described and sodium only in relation to hydrocracking catalysts. Furthermore, carryover of materials from the syngas or gas cleaning sections is not described. It has now been discovered that great care must be taken to avoid such carryover. Carryover through the syngas can be enhanced by the presence of steam. Certain materials used in syngas generation have been described by R. Stevens and U. R. Desai, Qatar Fertilizer Company, in the proceedings of Nitrogen+Syngas 2008 conference conducted in Moscow, 20-23 Apr. 2008. These include alumina lumps used in the upper part of the secondary reformer (ATR) that contain 0.7 wt % NaO, use of sodium aluminate, NaAl11O18 and a ceramic lining (donuts) that contains 17 wt % CaO.

SUMMARY OF THE INVENTION

It is generally an object of the present invention to provide an improved supported cobalt-based F-T catalyst. Further, it is an object of the present invention to avoid contamination of the catalyst during operation in an XTL plant, XTL being GTL (Gas to liquids), BTL (biomass to liquids) or CTL (coal to liquids). Contamination will lead to reduced catalytic performance, in particularly lower activity, resulting in need to replace the catalyst earlier than otherwise necessary.

According to one aspect of the present invention, there is provided a process for the preparation of a catalyst for a Fischer-Tropsch synthesis reaction, which comprises the following steps:

taking an initial porous support material selected from alumina, titania, zirconia, zeolites, carbonaceous material and mixtures thereof having an alkaline earth metal content of less than 1000 ppm;

impregnating the initial support material with a source of cobalt which contributes an additional alkaline earth metal content of less than 1000 ppm in the final catalyst; and heat treating the impregnated support material at a temperature of at least 200° C. to yield a cobalt oxide catalyst; whereby the final catalyst has an alkaline earth metal content of less then 2000 ppm.

The preparation of a cobalt catalyst involves impregnation of a support with a solution of a cobalt precursor, both of which may be a source of impurities. Water is a common choice as solvent. Water commonly contains significant amounts of minerals such as calcium, magnesium, and sodium. Controlling these elements is often necessary to meet the requirements of medical, pharmacology, chemical and industrial applications. Methods include distillation, filtration, water softening, reverse osmosis, ultrafiltration, molecular stripping, deionization, and carbon treatment.

DETAILED DESCRIPTION OF THE INVENTION

In general, the present invention is directed to the use of a Fischer-Tropsch catalyst in such a way that it is not exposed to unwanted components such as alkali and alkaline earth metals.

As has been shown, the catalyst should contain between 10 and 2000 ppm of alkaline earth or alkali metal, preferably between 20 and 1000 ppm, more preferably between 20 and 400 ppm. It is therefore important that the feed gas contains a correspondingly low content of these metals. A simplified calculation can be performed assuming an average operation of 10,000 hours (i.e. total of 20,000 hours between catalyst replacements), a productivity of 1.0 kg hydrocarbon product per kg catalyst per hour, and that all alkali or alkaline earth metals is picked up by the FT-catalyst. This surprisingly means that the alkali or alkaline earth content in the syngas feed should be as low as 100 ppb by weight (relative to kg CO in syngas) to yield below 2000 ppm on the catalyst. In other words, the syngas, frequently referred to as make-up gas in operations with a recycle of unconverted gas, should contain between 0.1 and 100 ppb, preferably between 0.5 and 50 ppb, more preferably between 0.5 and 20 ppb of alkali or alkaline earth as an average.

Such alkali or alkaline earth metal poisoning often takes place as a malfunction or upset in the operation, showing as a steep decline in catalyst activity over a shorter period of time, e.g. 10-1000 hours. Therefore, the alkali or alkaline earth metal content over such a period with enhanced poisoning should be kept in the range 5 ppb and 100 ppm, preferably between 10 ppb and 50 ppm, more preferably between 10 ppb and 20 ppm. Further, strict control of alkali and alkaline earth material should be in place during selection of any ceramic lining, reformer catalyst and guard bed materials, in addition to the content in process water and make-up water.

By controlling the levels of alkali and alkaline earth metals, an improved performance is achieved. The alkaline earth metals are those in Group 2 of the Periodic Table of the Elements and the invention is particularly concerned with calcium and magnesium, as well as sodium and potassium of Group 1.

Preferably, the heat treating step is a calcination step at a temperature in the range 200 to 600° C. The support material may be selected from alumina, silica, titania, zicinia, magnesia and zeolites and zeolite like materials, carbon in a variety of forms including carbon nanofibers and tubes, and mixtures and reaction products thereof, in any amorphous or crystallographic form, and optionally modified. The alumina may be γ-alumina, any transition alumina, α-alumina, boehmite, aluminium hydroxide or mixtures thereof.

The most preferred method of preparing alumina for the support is the alkoxide route, since it provides a high degree of purity. The precipitation method may also be adopted, and if so, the precipitated alumina should be washed with excess water several times to remove various impurities, such as alkali metals, alkali earth metals and sulphates. The water used should have a level of impurities including those mentioned of no more than 20 ppm. After washing, the alumina is preferably dried and optimally calcined at a temperature in the range 200 to 600° C.

Preferably, the initial alumina support material includes a stabilizer which preferably comprises lanthanum.

The impregnation step may comprise melt impregnation, ion-exchange, deposition/precipitation or more preferably, incipient wetness impregnation. In the case of the incipient wetness method, the solvent may be an organic solvent or more preferably water. There may be more than one impregnation step.

It has been found, surprisingly, that some alkaline-earth metals affect the Fischer-Tropsch synthesis using cobalt catalyst in an adverse manner. In particular, amounts of 100 ppm (mg/l) Ca using incipient wetness impregnation has a clear negative effect on the activity of the catalyst. Larger amounts of calcium (200-1000 ppm) have a very strong detrimental effect. These quantities are not unusual for many raw (tap) water sources. For instance, hard water contains from 80-120 ppm Ca.

Where water is used in the impregnations and any other process steps of the present invention, the water may be treated in some way such as those indicated to ensure the stipulated limits of alkaline earth metal. Preferably, the water is distilled or de-ionized water.

Preferably, the impregnation step comprises an incipient wetness treatment in which an aqueous solution of cobalt metal is mixed with the modified alumina support material until the pores are filled and the impregnated support material is then dried, prior to calcination. Preferably the amount of aqueous solution used in the impregnation is 0.2-2 times larger then the measured pore volume of the catalyst support.

Preferably, the method includes additionally impregnating or co-impregnating the initial alumina support material with a promoter. Preferably, the promoter comprises platinum or rhenium. The preferred range of platinum promoter is between 0.001 and 0.5 wt %, preferably between 0.01 and 0.1 wt %. For Re, the preferred range is between 0.01 and 5 wt %, preferably between 0.1 and 1.0 wt %.

Preferably, where the promoter is rhenium the source of rhenium is preferably selected from perrhenic acid ($HReO_4$), ammonium perrhenate, rhenium halide(s) and rhenium carbonyl(s).

The source of cobalt may be selected from cobalt nitrate ($Co(NO_3)_2$), cobalt carbonate(s), cobalt (hexa)amine salt(s) and organic cobalt compounds. After the calcination step, the alumina-supported catalyst material is preferably activated.

Preferably, the impregnated support is dried at a temperature in the range 80 to 120° C. The subsequent calcination is preferably carried out at a temperature in the range 200 to 600° C.

After the calcination step, the alumina-supported catalyst material is preferably activated.

The activation step may comprise reduction of a substantial portion of the catalytically active metal compound present to the metal, and may be carried out by treating the catalyst material with a reducing gas, such as hydrogen and/or carbon monoxide, optionally mixed with an inert gas. The reduction may be carried out at an activation temperature of 250 to 500° C., preferably in the range of 300 to 450° C.

Prior to impregnating the support with a source of cobalt, the support material may be modified. This may be accomplished by first impregnating the support material with a source of divalent metal capable of forming a spinel compound (general formula $(X)(Y)_2O_4$, where X and Y are cations) with the support material.

Adding a di-valent metal compound to alumina followed by heat treatment can yield a spinel compound that then will constitute part of or the entire support. The divalent-metal can comprise cobalt, nickel, magnesium or zinc, but also other spinel forming elements can be used. The heat treatment can be at temperatures up to 900° C. to give the spinel, but for certain purposes temperatures between 900 and 1400° C., typically 950-1250° C. are advantageous.

The divalent metal is preferably therefore zinc, cobalt, magnesium or nickel and suitable sources may include corresponding nitrates. The divalent metal is preferably deployed in one or more impregnation steps using a suitable solvent, which may be an organic solvent, or more preferably, water.

As with the subsequent cobalt impregnation step previously described, the solvent preferably has an alkaline earth metal content of less than 20 ppm, and is preferably distilled or de-ionized water. The source of divalent metal preferably yields an additional alkaline earth metal content in the cobalt oxide catalyst of less than 500 ppm, preferably less than 300 ppm, more preferably less than 100 ppm.

After impregnation with the divalent metal, the support material is dried, washed (if required) and calcined in one or several steps up to 600° C., to decompose the source of a divalent metal essentially to form a divalent metal oxide, or a compound thereof. Thereafter, a high temperature calcination may be carried out at a temperature in the range 600 to 900° C. to form the spinel. If a particularly high strength support is required, the last calcination may be carried out at an even higher temperature, in the range of 900 to 1400° C., preferably 950 to 1250° C.

This treatment with the divalent metal produces a modified support material which can then be impregnated with cobalt, as previously described. This high temperature treatment will reduce the porosity of the support to give a modified support with a surface area of below 80 m²/g, typically 30-70 m²/g, as well as a pore volume below 0.5 ml/g, typically between 0.15 and 0.4 ml/g. Although a high surface area is advantageous for maximizing the cobalt loading and dispersion and a high pore volume facilitates impregnation, the obtained values are perfectly acceptable in light of the much increased physical and chemical robustness of the modified support compared to the initial support.

It is also desirable to minimize the presence of alkali metals in the final catalyst, the alkali metals being those in Group 1 of the Periodic Table of the Elements. Preferably, therefore, the support material has an alkali metal content of less than 200 ppm, and any water used in the processing has an alkali metal content of less than 50 ppm, whereby the final catalyst has an alkali metal content of less than 250 ppm.

The present invention also extends to a catalyst material made in accordance with the process of the invention.

The present invention also extends to the use of such a catalyst in an F-T synthesis reaction, for example, carried out in a slurry bubble column reactor. In such a case, $H_2$ and CO are supplied to a slurry in the reactor, the slurry comprising the catalyst in suspension in a liquid including the reaction products of the $H_2$ and CO, the catalyst being maintained in suspension in the slurry at least partly by the motion of the gas supplied to the slurry.

The present invention also extends to a process for the production of hydrocarbons which comprises subjecting $H_2$ and CO gases to a Fischer-Tropsch synthesis reaction in a reactor in the presence of a supported Co-based catalyst in which make-up synthesis gas, comprising $H_2$ and CO, from a syngas generator is introduced into the system, the make-up synthesis gas containing less than 100 ppb of an alkaline earth metal or alkali metal.

The content of alkaline earth metal and/or alkali metal may for example, be between 0.1 and 100 ppb, preferably between 0.5 and 50 ppb, more preferably between 0.5 and 20 ppb, of an alkaline earth metal or alkali metal. The alkaline earth metal may be calcium and the alkali metal may be sodium.

Preferably, the reaction is a three-phase reaction in which the reactants are gaseous, the product is at least partially liquid and the catalyst is solid, and in which the reaction is carried out in a slurry bubble column reactor. In such a case, the $H_2$ and CO may be supplied to a slurry in the reactor, the slurry comprising the catalyst in suspension in a liquid including the reaction products of the $H_2$ and CO, the catalyst being maintained in suspension in the slurry at least partly by the motion of the gas supplied to the slurry.

Preferably, the make-up synthesis gas is passed through a guard bed of materials arranged to absorb components of alkali and alkaline earth metals from the synthesis gas stream, before the synthesis gas is subjected to a Fischer-Tropsch synthesis reaction. Preferably the guard bed comprises metal oxides, for example, alumina, silica, silica-alumina or zeolites, or magnesium or zinc oxides, or spent or deactivated catalysts supported on metal oxide materials. Alternatively, the guard bed comprises activated carbon or carbon nano fibres or tubes.

Typically, the reaction temperature is in the range 190-250° C., preferably, in the range 200-230° C. Typically, the reaction pressure is in the range 10-60 bar, preferably, the range 15 to 30 bar.

Typically, the $H_2$/CO ratio of the gases supplied to the Fischer-Tropsch synthesis reactor is in the range 1.1 to 2.2, preferably, in the range 1.5 to 1.95. Typically, the superficial gas velocity in the reactor is in the range 5 to 60 cm/s, preferably, in the range 20 to 40 cm/s.

The product of the Fischer-Tropsch synthesis reaction may subsequently be subjected to post-processing. The post-processing may comprise de-waxing, hydro-isomerization, hydrocracking and combinations of these.

The present invention also extends to a process for the production of hydrocarbons as discussed above, in which the catalyst is made by a process according to the present invention. Preferred and optional features of the process discussed above apply to this embodiment of the present invention as well.

The content of alkaline earth metal or alkali metal in the synthesis gas may be controlled by using feed containing low concentrations of alkaline earth metals and/or alkali metals. The water or steam which may be introduced or re-introduced as a reactant in the production of the synthesis gas, may be cleaned using one or more process selected from distillation, filtration, water softening, reverse osmosis, ultra-filtration, molecular stripping, de-ionization, and carbon treatment.

The lining of the reactors, tubing and equipment exposed to process streams in the production, transport and Fischer-Tropsch conversion of synthesis gas maybe made of materials resistant to giving off alkaline earth metals or alkali metals. The lining of the reactor may be a refractory or ceramic lining or a type of acid proof steal.

The surfaces of reactors, catalysts, tubing or other equipment exposed to process streams involved in the production and transport of synthesis gas and its conversion to hydrocarbons in a hydrocarbon-producing plant may be cleaned by removing alkali or alkaline earth metal substances from such surfaces before start-up of hydrocarbon production. Steam or water could, for example, be used for cleaning said surfaces The present invention may be carried into practice in various ways and will now be illustrated in the following non-limiting examples.

Catalyst Preparation

For all series of catalyst, high purity chemicals and solvents were used in the preparation.

Series A

The catalysts of series A contain a nominal amount of 20 wt % Co, 0.5 wt % Re and 0-1000 ppm Ca, as calculated assuming reduced catalysts with complete reduction of cobalt. The actual metal loading as determined by XRF or ICP may vary by up to 10%, e.g. for a catalyst with nominal loading of 20 wt %, the actual amount of cobalt can vary between 18 and 22 wt % of the total reduced catalyst weight. The catalysts were prepared by one-step incipient wetness co-impregnation of a $\gamma$-$Al_2O_3$ support (BET surface area=182 $m^2/g$, pore volume=0.73 $cm^3/g$) with aqueous solutions of cobalt nitrate hexahydrate, perrhenic acid and calcium nitrate tetahydrate.

The freshly prepared catalysts were dried for 3 h at a temperature of 110° C. During drying, the catalysts were stirred every 15 min during the first hour and every 30 min during the next two hours. After impregnation and drying, the samples were calcined at 300° C. for 16 h.

Series B

The catalysts of series B contain a nominal amount of 20 wt % Co, 0.5 wt % Re and 0-1000 ppm Ca, as calculated assuming reduced catalysts with complete reduction of cobalt. The supports were prepared by one-step incipient wetness impregnation of a $\gamma$-$Al_2O_3$ support (BET surface area=182 $m^2/g$, pore volume 0.73 $cm^3/g$) with aqueous solutions of calcium nitrate tetrahydrate. The supports were dried for 3 h at 110° C. During drying, the supports were stirred every 15 min during the first hours and every 30 min during the next two hours. After impregnation and drying, the modified supports were calcined at 900° C. for 10 h.

The catalysts were prepared by one-step incipient wetness co-impregnation of the Ca-containing supports (BET surface area=107 $m^2/g$, pore volume=0.68 $cm^3/g$) with aqueous solutions of cobalt nitrate hexahydrate and perrhenic acid. The catalysts were dried in the same manner as for series A. The catalysts were finally calcined at 300° C. for 16 h.

Series C

The catalysts of series C contain a nominal amount of 20 wt % Co and 0.5 wt % Re, as calculated assuming reduced catalysts with complete reduction of cobalt. In addition, the catalysts contained 200 or 700 ppm of Ca originating from the alumina production process.

The catalysts were prepared by one-step incipient wetness co-impregnation of the Ca-containing supports (BET surface area=107 $m^2/g$, pore volume=0.68 $cm^3/g$) with aqueous solutions of cobalt nitrate hexahydrate and perrhenic acid. The supports were dried for 3 h at 110° C. During drying, the supports were stirred every 15 min during the first hour and every 30 min during the next two hours. The catalysts were finally calcined at 300° C. for 16 h.

Series D

The catalysts of series D contain a nominal amount of 20 wt % Co, 0.5 wt % Re and 0 or 500 ppm Ca, as calculated assuming reduced catalysts with complete reduction of cobalt. The catalysts were prepared by one-step incipient wetness co-impregnation of $SiO_2$ support with aqueous solutions of cobalt nitrate hexahydrate, perrhenic acid and calcium nitrate tetahydrate. The procedures were as for series A regarding impregnation, drying and calcination.

Series E

The catalysts of series E contain a nominal amount of 12 wt % Co, 0.3 wt % Re and 0 or 400 ppm Ca or Mg, as calculated assuming reduced catalysts with complete reduction of cobalt. The catalyst support was in all cases essentially Ni-spinel prepared by one-step incipient wetness impregnation of nickel nitrate hydrate on the initial $\gamma$-alumina support followed by drying and calcination at a hold temperature in the range 400-500° C. giving a support in nickel oxide on alumina form. This oxide support was subsequently exposed to high temperature treatment at 1000-1200° C. for 10-30 min. in a rotary calciner giving a modified support, and one analysis shows a content of 29 ppm Ca and 18 ppm Mg, small amounts that come in addition to the 400 ppm introduced later by impregnation. The modified support has a pore volume of 0.23 ml/g and a surface area of 50 $m^2/g$.

The catalyst was prepared by co-impregnation of cobalt and rhenium salts in aqueous solution on to the modified support followed by drying and calcination giving a catalyst in oxide form. Ca or Mg then was deliberately added to this oxide catalyst by aqueous incipient wetness impregnation of the nitrate salts followed by drying for 3 h at 110° C. During drying, the supports were stirred every 15 min during the first hour and every 30 min during the next two hours. The Mg or Ca doped catalysts were finally calcined at 300° C. for 16 h.

Hydrogen Chemisorption

Hydrogen adsorption isotherms were recorded on a Micromeritics ASAP 2010 unit at 40° C. The samples were reduced in situ in flowing hydrogen at 350° C. for 16 h. The temperature was increased by 1 K/min from ambient to 350° C. An adsorption isotherm was recorded in the pressure interval 20 to 510 mmHg. The amount of chemisorbed hydrogen was calculated by extrapolating the linear part of the isotherm to zero pressure. In order to calculate the cobalt surface area, it was assumed that two cobalt sites were covered by one hydrogen molecule and that the area of one cobalt atom is $6.62 \cdot 10^{-22}$ $m^2$.

Catalyst Testing

The fixed bed testing was performed in a laboratory unit with four parallel fixed-bed reactors. 1 g of catalyst particles in a size fraction between 53 and 90 microns was mixed with 20 g of inert SiC. Reduction was performed in situ at 350°

C. for 16 h in hydrogen before a mixture of hydrogen and CO at ratio 2:1 was added. After 20 h on stream at 210° C. and 20 bar total pressure, the space velocity was adjusted to give an estimated conversion level of CO between 45 and 50% after 100 h. It is very important to perform selectivity, as well as activity, comparisons at the same level of conversion, as the level of steam generated in the reaction has a profound influence on the catalyst performance.

Results

Series A

The Fischer-Tropsch synthesis performance of the catalyst of series A is given in Table 1. In this case, Ca was deliberately added to the catalysts and the results are compared to the situation in which no calcium is added. It is clear that the relative activity decreases strongly with increasing calcium amount. Addition of 1000 ppm (0.1 wt %) Ca decreases the activity by 50%. However, the cobalt surface area ($m^2$/g catalyst) measured ex situ of all catalysts is, within experimental error, similar. Ca does not only affect the relative activity of the catalysts, but also the $C_{5+}$ selectivity; as shown in Table 1, addition of Ca decreases the $C_{5+}$ selectivity. Thus, Ca affects both the activity and selectivity in an unfavorable manner.

TABLE 1

Properties and catalytic data of the catalysts of series A. All contain 20 wt % Co, 0.5 wt % Re, and 0-1000 ppm Ca. Ca was co impregnated with cobalt and rhenium.

| Catalyst | Calcium amount (ppm) | Cobalt Surface area ($m^2$/g) | Relative activity | Relative $C_{5+}$ selectivity |
|---|---|---|---|---|
| A1 | 0 | 12.4 | 1.48 | 0.929 |
| A2 | 100 | | 1.30 | 0.914 |
| A3 | 500 | | 0.92 | 0.918 |
| A4 | 1000 | 13.2 | 0.75 | 0.910 |

As described above, the calcium can originate from impurities in the make-up syngas, and clearly deposition of such an impurity will have a negative effect on catalyst performance. In Table 2, it is assumed that operation is over 10,000 h (i.e. total of 20,000 hours between catalyst replacements), that productivity is of 1.0 kg HC/per kg catalysts, and that all of the calcium present in the syngas is picked up by the catalyst. As shown in Table 2, a concentration of 50 ppb Ca in the syngas decreases the activity by 50%.

TABLE 2

Properties and catalytic data of the catalysts of series A. simulating calcium being picked-up from the syngas. All contain 20 wt % Co, 0.5 wt % Re.

| Catalyst | Ca amount in syngas (ppb) | Corresponding Ca amount in catalyst (ppm) | Relative activity |
|---|---|---|---|
| A1 | 0 | 0 | 1.48 |
| A2 | 5 | 100 | 1.30 |
| A3 | 25 | 500 | 0.92 |
| A4 | 50 | 1000 | 0.75 |

Series B

Table 3 shows the catalytic data of the catalysts of series B. For these catalysts, calcium was added to the support. After the γ-$Al_2O_3$ supports were impregnated with the calcium precursor solutions, the samples were dried and subsequently calcined at 1173 K for 10 h. Thus, most of the calcium is probably present as calcium aluminate. However, just as for the catalysts of series A, calcium is detrimental for the catalyst activity. The $C_{5+}$ selectivity also decreases when Ca is added.

TABLE 3

Properties and catalytic data of the catalysts of series B. All contain 20 wt % Co, 0.5 wt % and 0-1000 ppm Ca. Ca was added to the support.

| Catalyst | Calcium amount (ppm) | Cobalt surface area ($m^2$/g) | Relative activity | Relative $C_{5+}$ selectivity |
|---|---|---|---|---|
| B1 | 0 | 12.6 | 1.51 | 0.930 |
| B2 | 500 | | 1.07 | 0.930 |
| B3 | 1000 | | 0.75 | 0.906 |

Series C

The calcium content of the catalysts of series C originates from the preparation process. Thus, no external Ca was added to these catalysts. Similar to series A and B, the activity and $C_{5+}$ selectivity decreases with increasing calcium concentration (Table 4).

TABLE 4

Properties and catalytic data of the catalysts of series C. All contain 20 wt % Co, 0.5 wt % Re and 0-700 ppm Ca. Ca was inherent in the alumina at levels of 200 and 700 ppm and the results are compared with the case where no Ca was present in the alumina.

| Catalyst | Calcium amount (ppm) | Cobalt surface area ($m^2$/g) | Relative activity | Relative $C_{5+}$ selectivity |
|---|---|---|---|---|
| A1 | 0 | | 1.48 | 0.929 |
| C1 | 200 | | 0.89 | 0.916 |
| C2 | 700 | | 0.81 | 0.897 |

Figure 1:
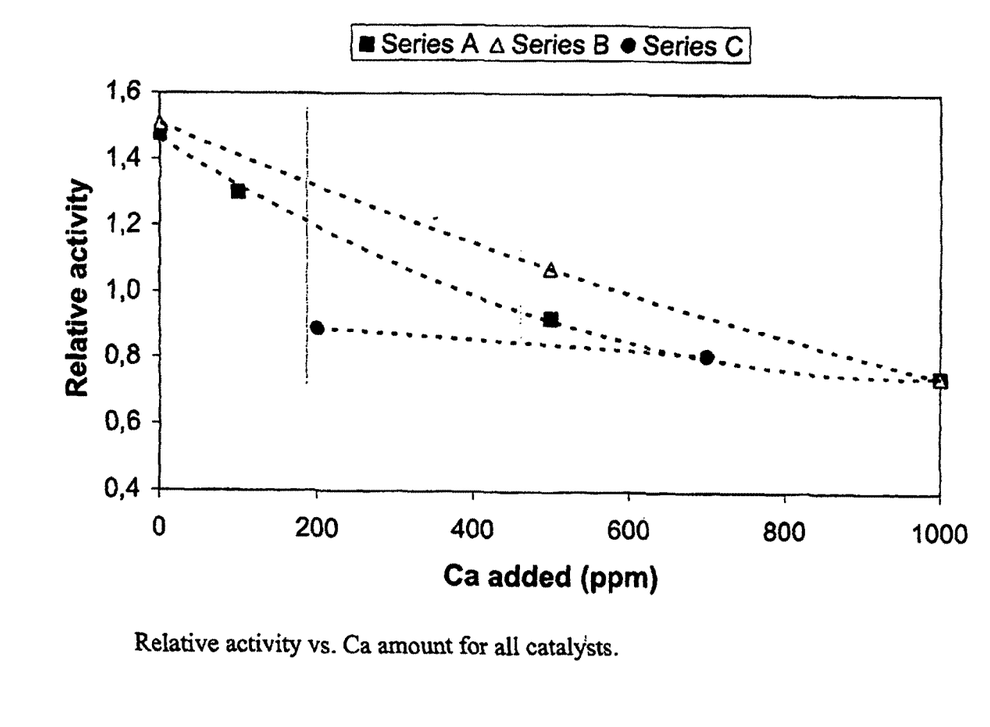
FIG. 1 shows graphically data from catalysts in Series A, B and C of the described catalyst preparation.

The diagram in FIG. 1 is a graphical representation of the data obtained for the catalysts in the Series A to C tests and shows how catalyst activities decrease as a result of rising concentration of calcium in the tested catalysts. The comparably low activity value obtained for the C1 catalyst (Ca concentration of 200 ppm) in the C1 series of test results may be due to the intrinsic dispersion of calcium in the catalyst support and the unknown nature and concentration of other impurities.

Series D

The Fischer-Tropsch synthesis performance of the catalyst of series D is given in Table 5. Ca was deliberately added to the catalyst by co-impregnation with cobalt and rhenium on a silica support and the results are compared to the situation in which no calcium is added. Also for these catalysts, the relative activity decreases strongly with increasing calcium amount. Addition of Ca also lowered the $C_{5+}$ selectivity. However, by comparing the results for 500 ppm Ca in Tables 1 and 5, it is surprising that alumina is more robust towards alkaline earth, in particular calcium, poisoning than silica. Alumina is therefore a more preferred support material than silica.

TABLE 5

Properties and catalytic data of the catalysts of series D. All contain 20 wt % Co, 0.5 wt % Re, and 0-500 ppm Ca. Ca was co impregnated with cobalt and rhenium on a silica support.

| Catalyst | Calcium amount (ppm) | Relative activity | Relative $C_{5+}$ selectivity |
|---|---|---|---|
| D1 | 0 | 1.36 | 0.957 |
| D2 | 500 | 0.44 | 0.951 |

Series E

The Fischer-Tropsch synthesis performance of the catalysts of series E is given in Table 6. In this case the support essentially was Ni-spinel, and the catalyst was prepared by co-impregnation of cobalt and rhenium salts in aqueous solution followed by drying and calcination, giving a catalyst in oxide form. Ca or Mg then was deliberately added to this oxide catalyst by impregnation. Also for these catalysts, the relative activity decreases strongly with increasing calcium or magnesium amount, but to a lesser extent for magnesium.

Note that adding the impurity element to the catalyst closely resembles a situation where the impurity is introduced by make-up syngas, ref. Table 2 with 25 ppb calcium in syngas, and then picked-up by the catalyst.

TABLE 6

Properties and catalytic data of the catalysts of series D. All contain 12 wt % Co, 0.3 wt % Re, and 0-500 ppm Ca or Mg. The latter was impregnated on the oxide catalyst.

| Catalyst | Calcium or magnesium amount (ppm) | Relative activity | Relative $C_{5+}$ selectivity |
|---|---|---|---|
| E1 | 0 | 0.96 | 0.915 |
| E2 | 400 (Ca) | 0.49 | 0.894 |
| E3 | 400 (Mg) | 0.76 | 0.908 |

When calcium is added as a poison to the catalyst, calcium is expected to be distributed on the available surface of the catalyst. For the Co/Re/γ-alumina catalyst with 500 ppm Ca this area is 135 m²/g, whereas for the Co/Re/NiAL₂O₄ catalyst the area is 46 m²/g. We therefore may expect the poisonous effect for the latter catalyst to be stronger, for example 135/46=2.9 times stronger. However, the effect of 500 ppm Ca on Co/Re/γ-alumina is a 37% reduction in activity compared to a 41% reduction for 400 ppm Ca on Co/Re/NiAL₂O₄, in other words a moderate difference. We therefore observe that the catalyst with a spinel support is more robust towards poisoning for a given surface area. The same argument holds if we instead of the difference in total surface area use the difference in cobalt loading, 20 vs. 12% for the two catalysts, or cobalt surface area. Again the spinel catalyst is more robust towards calcium poisoning per Co loading.

The invention claimed is:

1. A catalyst for a Fischer-Tropsch synthesis reaction made by taking an initial alumina porous support material having an alkaline earth metal content of less than 1000 ppm, wherein the initial alumina support material is modified by treatment with a divalent metal which is capable of forming a spinel and is calcined at a temperature in the range of 900 to 1400° C. such that the modified support comprises a spinel compound, wherein the modified support material is impregnated with a source of cobalt in the form of a cobalt precursor, which contributes an additional alkaline earth metal content of less than 1000 ppm in the final catalyst, wherein the impregnated support material is heat treated at a temperature of at least 200° C. to yield a cobalt oxide catalyst, and wherein the catalyst comprises:
a porous support material, an active cobalt content of 5 to 60 wt % expressed in terms of weight of the catalyst as a whole, assuming complete reduction of the cobalt precursor to cobalt metal, and an alkaline earth metal content of less than 2000 ppm.

2. The catalyst for a Fischer-Tropsch synthesis reaction of claim 1, wherein the support material is γ-alumina, any transition alumina, α-alumina, boehmite, aluminium hydroxide or mixtures thereof.

3. The catalyst for a Fischer-Tropsch synthesis reaction of claim 1, wherein the support material is alumina and is prepared by the precipitation method or the alkoxide route.

4. The catalyst for a Fischer-Tropsch synthesis reaction of claim 1, wherein the support material is γ-alumina, and is prepared by heating to a temperature in the range 400 to 800° C.

5. The catalyst for a Fischer-Tropsch synthesis reaction of claim 1, wherein the initial support material has an alkaline earth metal content of less than 500 ppm.

6. The catalyst for a Fischer-Tropsch synthesis reaction of claim 1, wherein the initial support material has an alkaline earth metal content of between 5 and 1000 ppm.

7. The catalyst for a Fischer-Tropsch synthesis reaction of claim 1, wherein the alkaline earth metal is calcium or magnesium.

8. The catalyst for a Fischer-Tropsch synthesis reaction of claim 1, further comprising a stabilizer incorporated into the porous support material.

9. The catalyst for a Fischer-Tropsch synthesis reaction of claim 8, wherein the stabilizer is lanthanum.

10. The catalyst for a Fischer-Tropsch synthesis reaction of claim 1, wherein the cobalt is selected from cobalt nitrate ($Co(NO_3)_2$), cobalt carbonate(s), cobalt (hexa) amine salt(s) and organic cobalt compounds.

11. The catalyst for a Fischer-Tropsch synthesis reaction of claim 1, wherein the support material comprises a promoter.

12. The catalyst for a Fischer-Tropsch synthesis reaction of claim 11, wherein the promoter comprises platinum or rhenium.

13. The catalyst for a Fischer-Tropsch synthesis reaction of claim 12, wherein the promoter is platinum and represents between 0.001 and 0.5 wt %.

14. The catalyst for a Fischer-Tropsch synthesis reaction of claim 12, wherein the promoter is rhenium and represents between 0.01 and 5 wt %.

15. The catalyst for a Fischer-Tropsch synthesis reaction of claim 12, wherein the promoter is rhenium and the source of rhenium is selected from perrhenic acid ($HReO_4$), ammonium perrhenate, rhenium halide and rhenium carbonyl(s).

16. The catalyst for a Fischer-Tropsch synthesis reaction of claim 1, wherein the divalent metal is nickel or zinc or mixtures thereof.

17. The catalyst for a Fischer-Tropsch synthesis reaction of claim 16, wherein the source of nickel is nickel nitrate, and/or the source of zinc is zinc nitrate.

18. The catalyst for a Fischer-Tropsch synthesis reaction of claim 1, wherein the divalent metal is deployed in one or more impregnation steps using a solvent, yielding from the impregnation step an alkaline earth metal content of less than 500 ppm in the cobalt oxide catalyst.

19. The catalyst for a Fischer-Tropsch synthesis reaction of claim 1, wherein the divalent metal is deployed in one or more impregnation steps using a solvent, yielding from the impregnation step an alkaline earth metal content between 5 and 500 ppm.

20. The catalyst for a Fischer-Tropsch synthesis reaction of claim 1, wherein the support material has a specific surface area below 80 m²/g.

21. The catalyst for a Fischer-Tropsch synthesis reaction of claim 1, wherein the support material has a pore volume below 0.5 ml/g.

22. A Fischer-Tropsch catalyst comprising:
a cobalt source impregnated on a porous support material;
wherein the porous support material comprises alumina and a divalent metal spinel; said porous support material being prepared by modifying an initial alumina support material by treatment with a source of a divalent metal which is capable of forming a spinel and calcining the treated support material at a temperature in the range of 900 to 1400° C. to yield the divalent metal spinel and
wherein said catalyst has an alkaline earth metal content of less than 2000 ppm.

23. The Fischer-Tropsch catalyst of claim 22, wherein the support material is alumina and is prepared by the precipitation method or the alkoxide route.

24. The Fischer-Tropsch catalyst of claim 22, wherein the support material is gamma-alumina, any transition alumina, alpha-alumina, boehmite, aluminium hydroxide or mixtures thereof.

25. The Fischer-Tropsch catalyst of claim 24, wherein the support material is gamma-alumina, the gamma-alumina prepared by heating to a temperature in the range of 400° C. to 800° C.

26. The Fischer-Tropsch catalyst of claim 22, wherein the divalent metal comprises cobalt, nickel, magnesium or zinc.

27. The Fischer-Tropsch catalyst of claim 22, wherein the divalent metal is nickel or zinc or mixtures thereof.

28. The Fischer-Tropsch catalyst of claim 27, wherein the divalent metal is nickel from a source of nickel nitrate.

29. The Fischer-Tropsch catalyst of claim 27, wherein the divalent metal is zinc from a source of zinc nitrate.

30. The Fischer-Tropsch catalyst of claim 22, wherein the porous support material has an alkaline earth metal content of less than 500 ppm.

31. The Fischer-Tropsch catalyst of claim 22, wherein the porous support material has an alkaline earth metal content of between 5 and 1000 ppm.

32. The Fischer-Tropsch catalyst of claim 22, wherein the alkaline earth metal is calcium or magnesium.

33. The Fischer-Tropsch catalyst of claim 22, further comprising a stabilizer incorporated into the porous support material.

34. The Fischer-Tropsch catalyst of claim 33, wherein the stabilizer is lanthanum.

35. The Fischer-Tropsch catalyst of claim 22, further comprising a promoter.

36. The Fischer-Tropsch catalyst of claim 35, wherein the promoter comprises platinum or rhenium.

37. The Fischer-Tropsch catalyst of claim 36, wherein the promoter is platinum and represents between 0.001 and 0.5 wt %.

38. The Fischer-Tropsch catalyst of claim 36, wherein the promoter is rhenium and represents between 0.01 and 5 wt %.

39. The Fischer-Tropsch catalyst of claim 36, wherein the promoter is rhenium and the source of rhenium is selected from perrhenic acid ($HReO_4$), ammonium perrhenate, rhenium halide and rhenium carbonyl(s).

40. The Fischer-Tropsch catalyst of claim 22, wherein the cobalt source is in an oxidated state.

41. The Fischer-Tropsch catalyst of claim 22, wherein the cobalt is an activated cobalt.

42. The Fischer-Tropsch catalyst of claim 22, wherein the source of cobalt is selected from cobalt nitrate ($Co(NO_3)_2$), cobalt carbonate(s), cobalt (hexa) amine salt(s) and organic cobalt compounds.

43. The Fischer-Tropsch catalyst of claim 22, wherein the porous support material comprises a divalent metal yielding an alkaline earth metal content of less than 500 ppm.

44. The Fischer-Tropsch catalyst of claim 22, wherein the porous support material comprises a divalent metal yielding an alkaline earth metal content between 5 and 500 ppm.

45. The Fischer-Tropsch catalyst of claim 22, wherein the porous support material has a specific surface area below 80 m²/g.

46. The Fischer-Tropsch catalyst of claim 22, wherein the porous support material has a pore volume below 0.5 ml/g.

* * * * *